United States Patent [19]

Miyao

[11] Patent Number: 5,080,587
[45] Date of Patent: Jan. 14, 1992

[54] INSTRUMENT FOR DISCHARGING WATER IN THE MOUTH FOR DENTAL TREATMENT

[76] Inventor: Hyoichyro Miyao, 14-4 Asahichyro 2-chome, Nerima-ku, Tokyo, Japan

[21] Appl. No.: 622,225

[22] Filed: Dec. 3, 1990

Related U.S. Application Data

[63] Continuation-in-part of Ser. No. 385,550, Jul. 26, 1989, abandoned.

[30] Foreign Application Priority Data

Jul. 30, 1988 [JP] Japan .................. 63-101388

[51] Int. Cl.$^5$ .................. A61C 17/06; A61C 17/14
[52] U.S. Cl. ............................ 433/91; 433/96
[58] Field of Search ............... 433/91, 93, 94, 95, 433/96

[56] References Cited

U.S. PATENT DOCUMENTS

| | | | |
|---|---|---|---|
| 950,109 | 2/1910 | Lenkowicz | 433/91 |
| 1,222,267 | 4/1917 | Cosad | 433/91 |
| 3,084,440 | 4/1963 | Wenof | 433/96 |
| 3,101,544 | 8/1963 | Baughan | 433/94 |
| 3,758,950 | 9/1973 | Krouzian | 433/91 |
| 3,807,401 | 4/1974 | Riggle et al. | 433/91 X |
| 3,864,831 | 2/1975 | Drake | 433/91 |
| 4,017,975 | 4/1977 | Johnson | 433/91 X |
| 4,068,664 | 1/1978 | Sharp et al. | 433/91 X |
| 4,158,916 | 6/1979 | Adler | 433/91 |
| 4,521,185 | 6/1985 | Cohen | 433/93 X |

FOREIGN PATENT DOCUMENTS 2621767 2/1976 Fed. Rep. of Germany ........ 433/91

Primary Examiner—Robert P. Swiatek
Assistant Examiner—Nicholas D. Lucchesi
Attorney, Agent, or Firm—Notaro & Michalos

[57] ABSTRACT

An instrument for discharging water from the mouth during a dental treatment, has an ovoid, smooth-surface, edge free hollow water collection body with a front surface facing outwardly of the mouth and a rear surface facing toward the throat inlet of the mouth. Two rows of orifices are provided on the rear surface and alternately on the rear and front surfaces for receiving a water mixture from the patient's mouth. A mounting tube projects from the front surface and at at an angle to the axis of the body for connection to a water discharge tube for drawing water from the body.

2 Claims, 7 Drawing Sheets

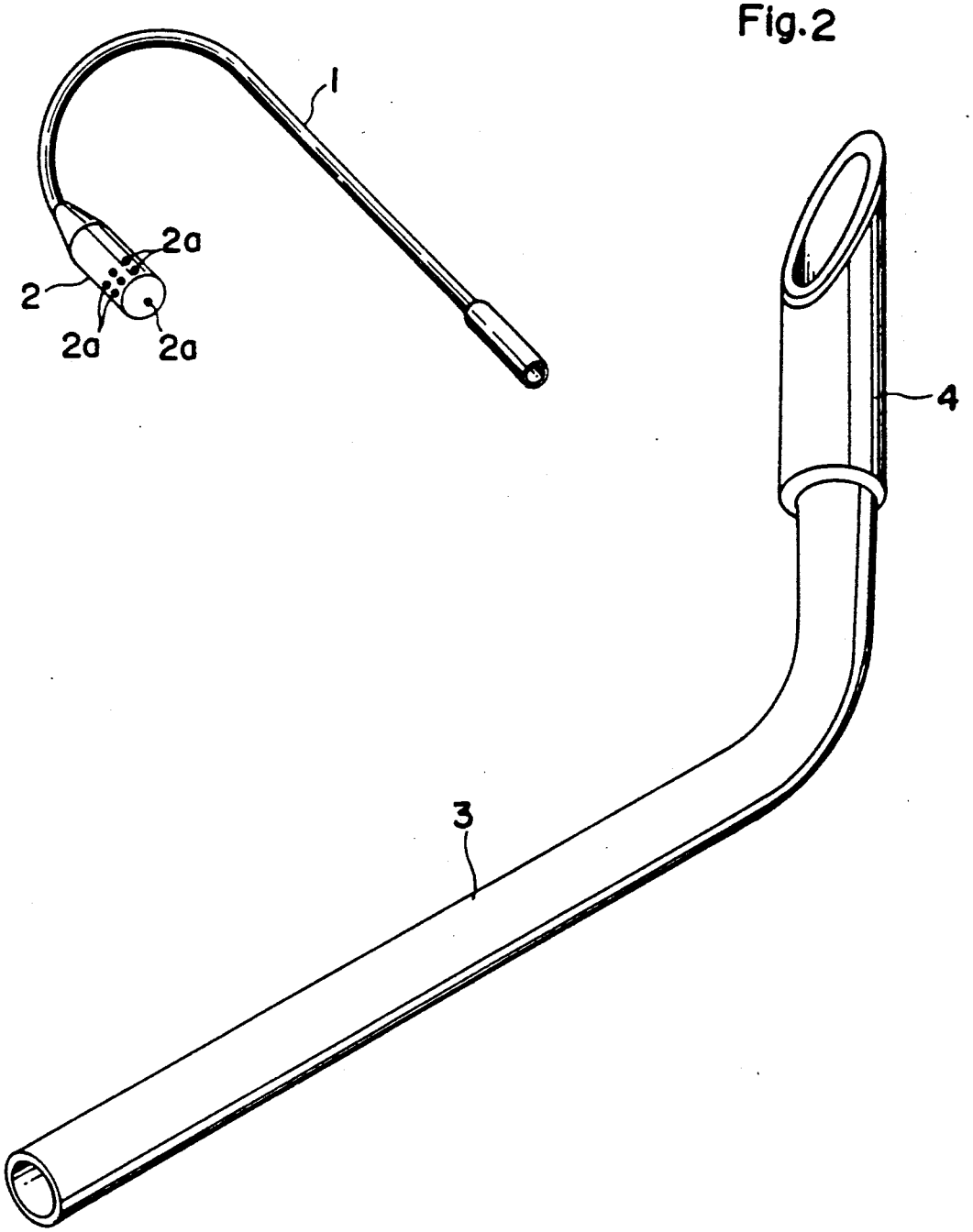

5,080,587

INSTRUMENT FOR DISCHARGING WATER IN THE MOUTH FOR DENTAL TREATMENT

This application is a continuation-in-part of application Ser. No. 385,550, filed July 26, 1989, now abandoned.

BACKGROUND OF THE INVENTION

1. Field of the Invention

This invention relates to an instrument for discharging water from the mouth during a dental treatment, which is suitably used for always discharging the mixed water and saliva which is at a deep portion of the mouth during treatment of teeth.

2. Description of the Prior Art

During treatment of the teeth, means are needed to remove saliva, medical liquid, cold washing water for cooling the teeth and removing cutting and polishing material and debris from the affected areas. This water mixture would otherwise stay in the deep portion of the mouth and choke the patient. The water mixture also disturbs the dentist in his treatment and in addition inflicts discomfort on the patient who feels like the mixture is being force down his throat. The devices shown in FIGS. 1 and 2 are known for removing this water mixture from the mouth.

The device shown in FIG. 1 is called a saliva-discharge tube. The whole saliva-discharge tube 1 has an approximately U-shape, to which end is mounted a saliva-collection tube 2 provided with orifices 2a.

The device shown in FIG. 2 is called a water suction tube. The whole water suction tube 3 having a relatively large diameter has an approximately <-shape, to which is mounted a water collection tube 4 formed from a soft rubber tube.

In the device shown in FIG. 1, since an aperture of the saliva discharge tube 1 is small, this will not obstruct the treatment of teeth. But, the tube 1 is weak in suction force and in addition, the saliva collection tube 2 is also small and the distance from the bent position of the U-shape to the saliva collection tube 2 is short. Therefore, the saliva collection tube 2 does not reach the deep portion in the mouth, which is extremely insufficient to discharge the mixed water.

In the device shown in FIG. 2, an assistant holds the water suction tube 3 during treatment of the teeth and places the water collection tube 4 at appropriate positions to collect the water mixture. Water cannot be completely discharged merely by the arrangement as just mentioned and the mixed water cannot be prevented from staying in the deep portion in the mouth. Therefore, the treatment has to be often discontinued so that the patient may discharge the liquid. Furthermore, if the water collection tube 4 is inserted into the deep portion in the mouth, the sharp sense at the deep portion of the mouth stimulates the patient who feels like vomiting. For this reason the tube 4 is not used near the deep portion of the patient's mouth.

OBJECT OF THE INVENTION

An object of this invention is to provide an instrument for discharging water and saliva from the mouth for dental treatment which can always effectively discharge the mixed water in a deep portion of the mouth during the treatment of teeth while treating the teeth without having the patient feel like vomiting. The invention avoids forcing the mixed water down the patient's throat and can minimize discontinuation of treatment due to patient discomfort.

A further object of this invention is to provide an instrument for discharging water from the mouth for dental treatment in which a consideration is given so that in order to reduce a feeling of physical discomfort, the water collection body which is placed at the throat of the patient, is formed of a soft elastic material and is ovoid and edge-free in shape.

A further object of this invention is to provide an instrument for discharging water from the mouth for dental treatment in which the device is made so that even if a water discharge tube is connected to a saliva discharge tube having a weak attraction force, the water discharge tube can sufficiently exhibit its water discharging function.

Another object of this invention is to provide an instrument for discharging water from the mouth for dental treatment in which the device is made so that a position of the body in the mouth is held by a tube for extracting water from the body.

According to another embodiment of the invention, the water collection body is formed of a hard or semi-hard material and has a smooth surface.

According to the invention, a mounting portion of the water discharge tube is mounted on one side of the water collection body.

According to the invention, in mounting the mounting portion of the water discharge tube on one side of the water collection body, the mounting portion of the water discharge tube is bent toward the water collection body.

BRIEF DESCRIPTION OF THE DRAWINGS

FIG. 1 is a perspective view of a conventional saliva discharge tube used for discharging saliva in the mouth;

FIG. 2 is a perspective view of a conventional water suction tube used for sucking water in the mouth;

DETAILED DESCRIPTION OF THE PREFERRED EMBODIMENTS

Figure 3:
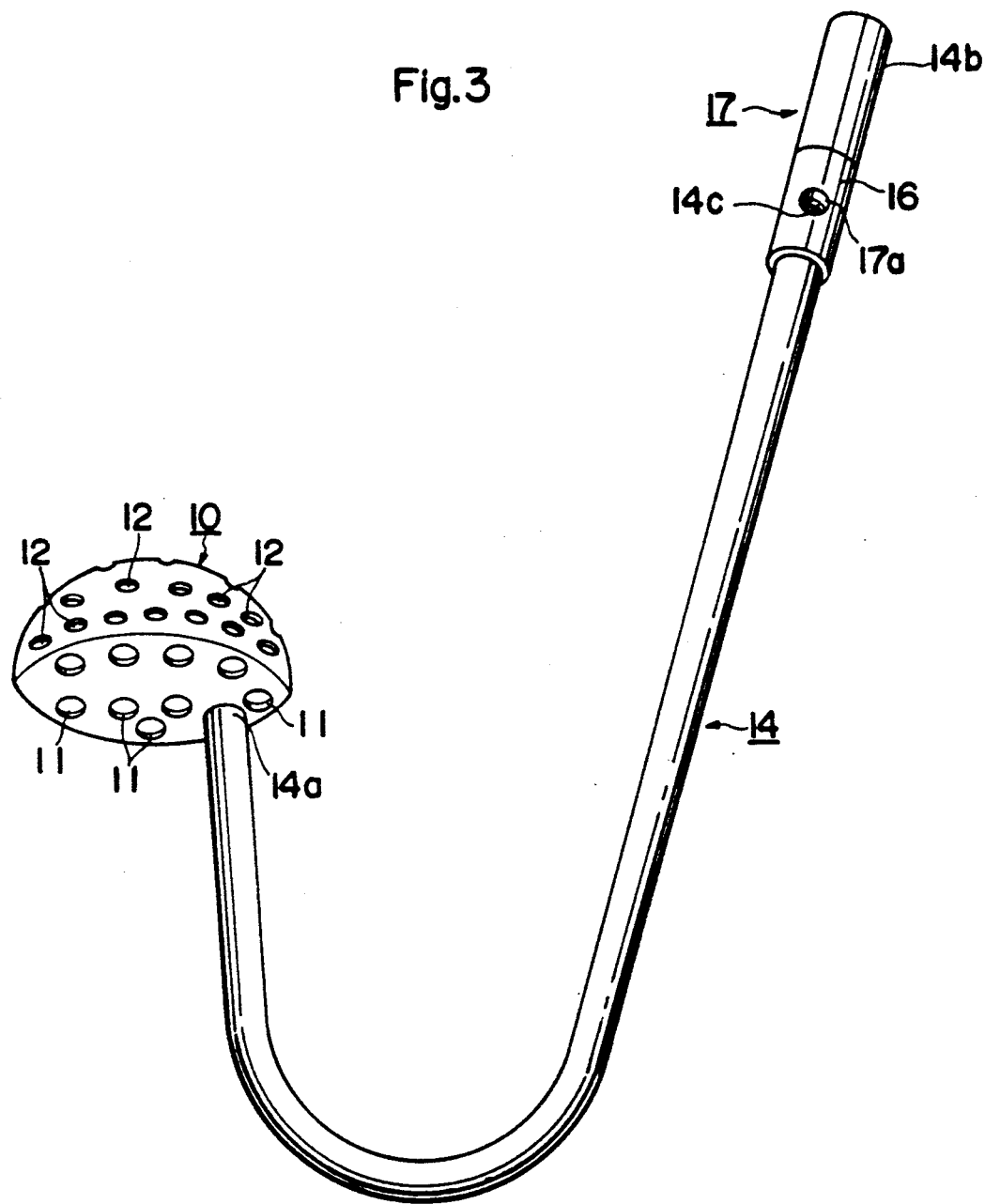
FIG. 3 is a perspective view showing one embodiment of this invention.
Figure 4:
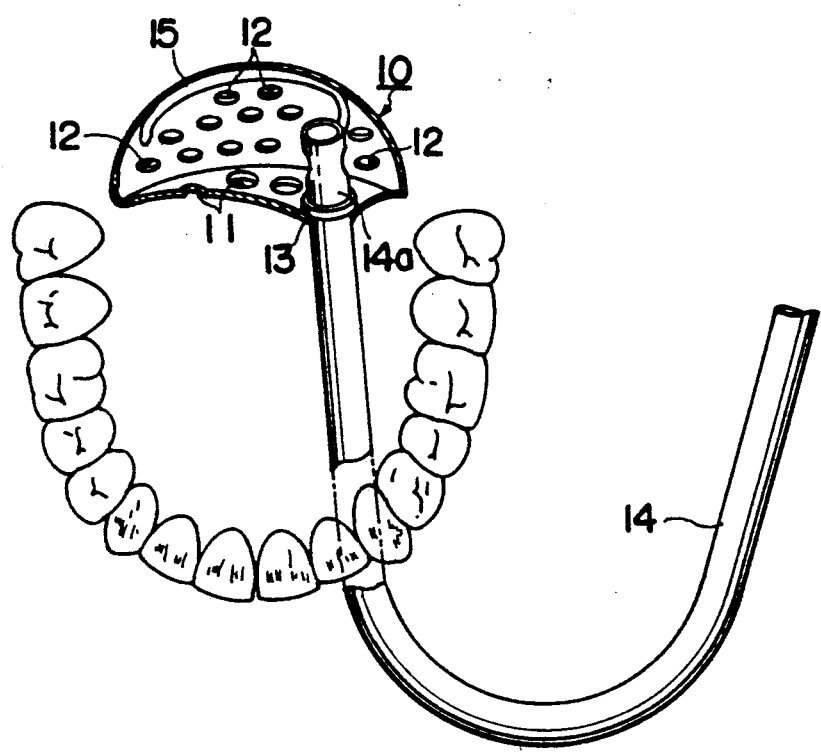
FIG. 4 is a plan view partly cutaway and partly in section showing an example of use for the invention.

Referring now to FIGS. 3 and 4, reference numeral 10 designates a hollow bag-like water collection body formed of soft and resilient rubber such as latex rubber, the water collection body having a boat-like shape in plane. The water collection body 10 is sufficiently elastic and resilient to have a self-restoring capability when it is pressed and collapsed. The configuration of the body 10 is not limited to that shown in the embodiment but other spherical or elliptic configurations or the like may be employed.

The water collection body 10 is provided with a number of orifices 11 and 12 extending parallel to a long axis of the ovoid body. The orifices 11 provided on the front side of body 10 with respect to the mouth of a patient, are positioned to face outwardly of the mouth during use and are made slightly larger than the orifices 12 provided on an opposite rear side, positioned to face the throat. The orifices are large enough to easily gather water in collection body 10 and to minimize pain caused by the attraction of the body if it contacts tissue of the deep portion in the mouth. The water collection body 10 is particularly provided at one end thereof with a mounting hole 13 as shown in FIG. 4. A member having an approximately U-shape with a mounting portion 14a inserted into the mounting hole 13 forms a water discharge tube 14. In this embodiment, the water collection body 10 is mounted at a distance from the curved position of the water discharge tube which is determined so that the mounting portion 14a of the water discharge tube 14 reaches a position in the deep portion of the mouth where the water collection body 10 is best placed.

A shape-retention member 15 having an approximately arch-shape particularly as shown in FIG. 4 is mounted on the end of a portion of the water collection tube 14 which is inserted into the water collection body 10 to maintain its original shape and to prevent the water collection body 10 from collapsing during the discharge of water. The shape-retention member 15 is required when the water collection body 10 is formed of a soft material and is not sometimes required when the water collection body 10 is more resilient.

A connecting portion 14b for connecting a water discharge hose (not shown) is provided on the other end of the water discharge tube 14, particularly as shown in FIG. 3, the connecting portion 14b being provided with air intake means 16. The air intake means 16 comprises a vent hole 14c provided in the water discharge tube 14 and an air adjusting ring 17 in the form of a ring rotatably fitted on the outer periphery of the tube. The air adjusting ring 17 is provided with an air port 17a in registration with the vent hole 14c. The air intake means 16 is not required when the attraction force due to suction is weak.

In the embodiment in use, the water collection body 10 is placed just over the inlet of the throat in the deep portion of the mouth of a patient, as shown in FIG. 4, and a vacuum pump (not shown) is used to always discharge the mixed water during treatment.

Figure 5:
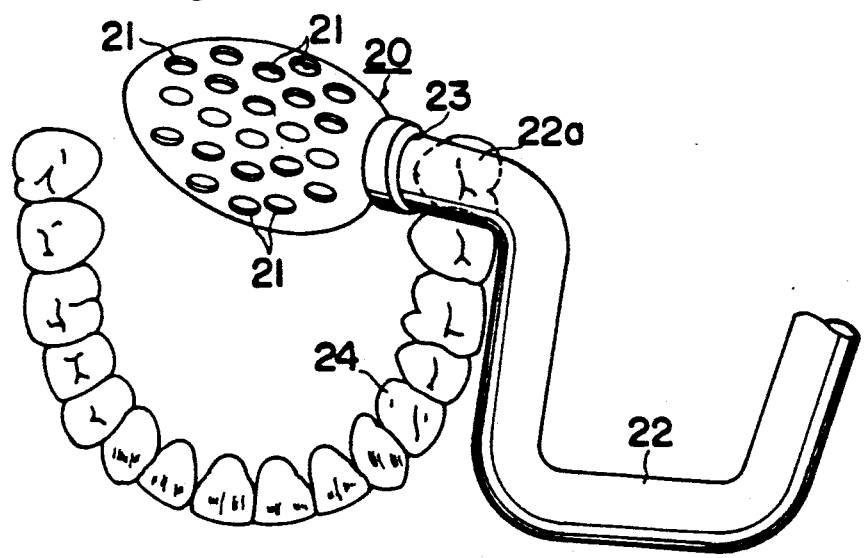
FIG. 5 is a partly cutaway plan view showing a further embodiment of the invention.

FIG. 5 shows another embodiment, which is the same as the previous embodiment in that the water collection body 20 is provided with a plurality of orifices 21. This embodiment is different from the previous embodiment in that the water collection body 20 itself is formed of hard or semi-hard material such as polyethylene, acryl, etc. The water discharge pipe 22 has a mounting portion 22a which is bent toward the water collection body 20 from a U-shaped portion of the pipe 22, a mounting portion 22a is inserted into and secured to a mounting hole 23 provided on one side of the water collection body 20. Of course, the mounting hole 23 would not be required in the case where the water collection body 20 and the water discharge tube 22 are integrally molded.

In this embodiment, as shown in FIG. 5, in use, the water discharge tube 22 is inserted into the mouth along a row of teeth 24, and the water collection body 20 can be easily arranged in the inlet of the throat in a central deep portion of the mouth.

In FIGS. 3 and 4, the mounting the water discharge tube on the water collection body can be embodied as in FIG. 5.

Figures 6, 7, 8:
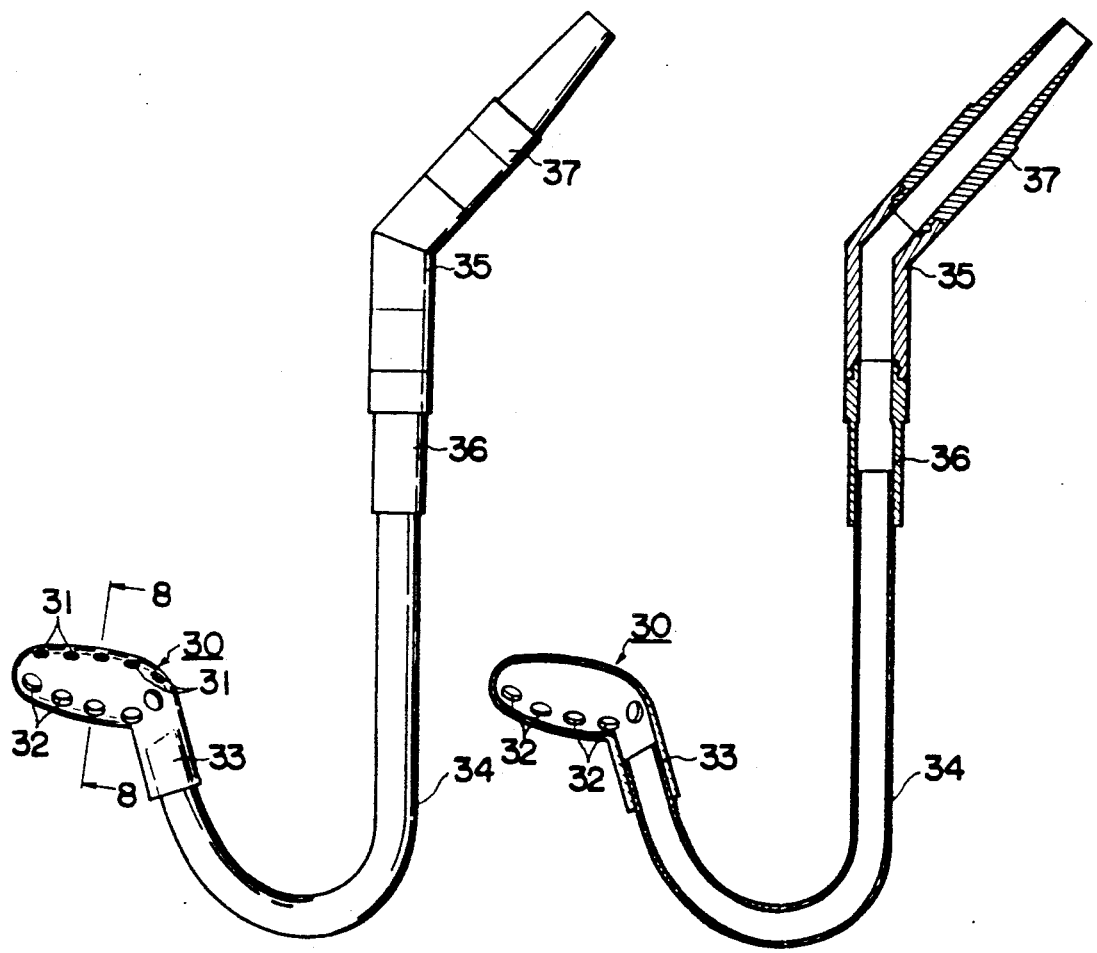
FIG. 6 is a plan view showing another embodiment of the invention.
FIG. 7 is a plan view in section of FIG. 6.
FIG. 8 is an enlarged sectional view taken on line 8—8 of FIG. 6.

FIGS. 6 to 8 show another embodiment. As shown, a water collection body 30 made of synthetic resin which is soft but resilient to have shape retention, is provided at the rear with two rows of plural orifices 31 and provided at the front with two rows of middle orifices 32 having larger diameter than the orifices 31. A tubular mounting body 33 projects on one side of the water collection body 30, and one end of a water discharge tube 34 having an approximately U-shape and a relatively large diameter is slidable and rotatably inserted into and secured to the tubular body 33. The water discharge tube 34 is connected to a mounting tube 36 of which the other end is connected axially rotatably to one end of an attitude control tube 35 having an approximately V-shape. The attitude control tube 35 has an other end to which is rotatably connected a tube connection tube 37, and a tube connected to vacuum (not shown) is connected to the tube connection tube 37.

The water discharge tube in this embodiment is connected to a vaccum having a powerful attraction force through a vacuum hose. However, since the water collection body 30 is provided with the middle orifices, the water collection body 30 is not collapsed by the attraction force.

Figure 9:
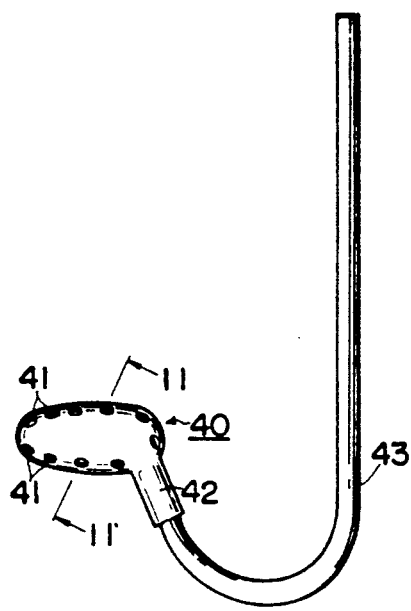
FIG. 9 is a plan view showing another embodiment of the invention.
Figure 10:
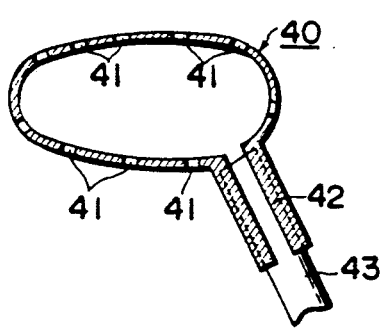
FIG. 10 is a partly enlarged plan view in section of FIG. 9.
Figure 11:
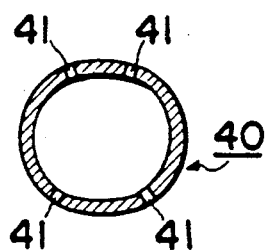
FIG. 11 is an enlarged sectional view taken on line 11—11 of FIG. 9.

FIGS. 9 to 11 show still another embodiment in which shape, size and material of the water collection body are the same as those shown in FIGS. 6 to 8. However, this water collection body 40 is provided at the front and rear with two rows of orifices 41 having approximately the same diameter. One end of a water discharge tube 43 having the same diameter as that of a conventional saliva discharge tube and having an approximately U-shape in plane is inserted into and secured to a mounting tubular body 42 having a smaller diameter than that of the previous embodiments. With this arrangement, since all the orifices have the same diameter, even if the water collection body is connected to the saliva discharge tube merely having a weak attraction force, it is possible to sufficiently discharge water in the deep portion in the mouth.

Figure 12:
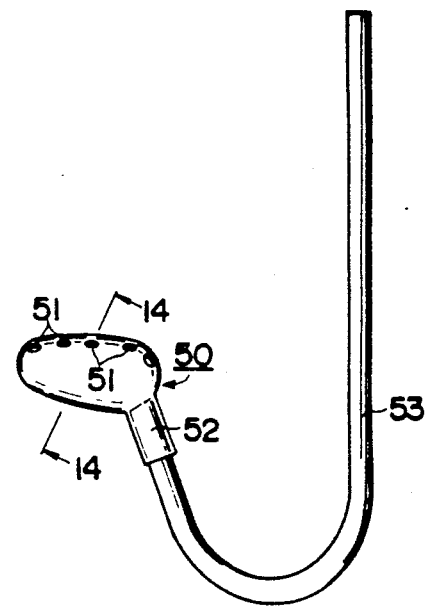
FIG. 12 is a plan view showing still another embodiment of the invention.
Figure 13:
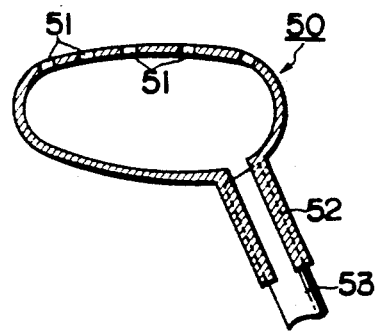
FIG. 13 is a partly enlarged plan view in section of FIG. 11.
Figure 14:
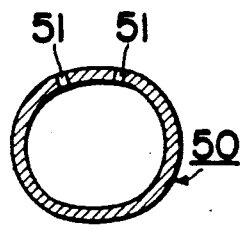
FIG. 14 is an enlarged sectional view taken on line 14—14 of FIG. 12.

FIGS. 12 to 14 show another embodiment. Also in this embodiment, the shape, size and material of a water collection body 50 are the same as those shown in FIGS. 6 to 8 but the water collection body 50 is provided only on one side thereof with orifices 51. Moreover, the water discharge tube 53 is inserted into the water collection body until it is near the orifice 51.

With this arrangement, even if a mounting tube 52 of the water collection body 50 is connected to a water discharge tube 53 having the same diameter as that of a conventional saliva discharge tube merely having a weak attraction force, it is possible to sufficiently discharge water and the water collection body is not collapsed by the attraction force despite the small number of orifices.

Figure 15:
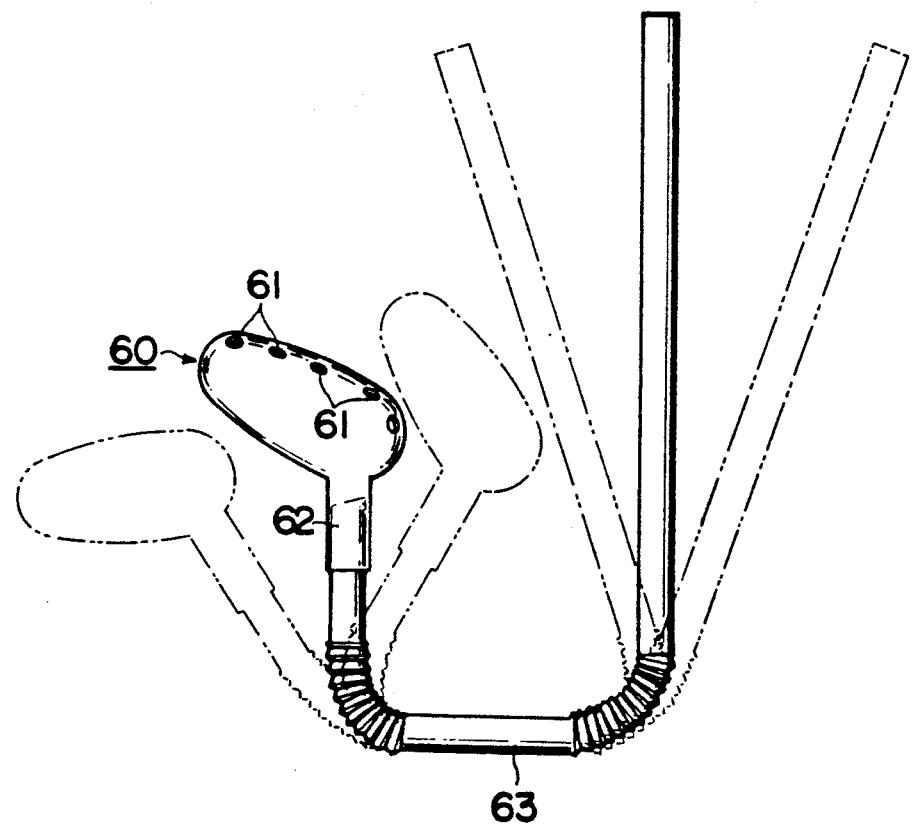
FIG. 15 is a plan view showing another embodiment of the invention.

FIG. 15 shows another embodiment, in which a water discharge tube 63 itself is flexibly bendably provided on a mounting tube 62 of a water collection body 60 provided on one side thereof with orifices 61.

With this arrangement, there is an advantage that the position of the water discharge tube (not shown) connected to the water discharge tube 63 during treatment of teeth can be freely changed without obstruction.

Figure 16:
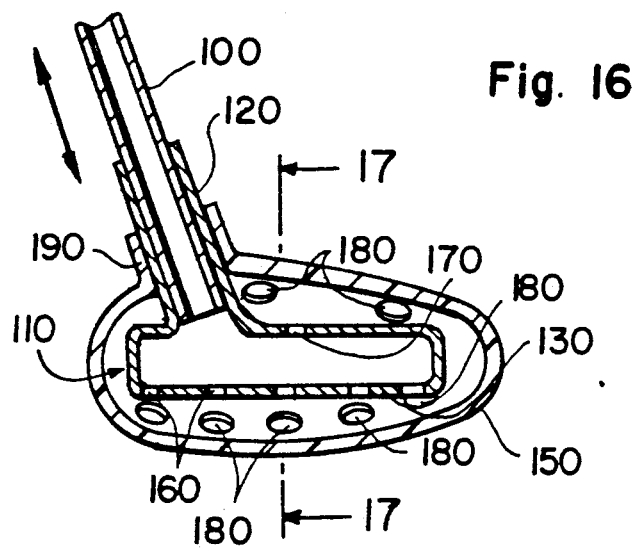
FIG. 16 is a sectional view of another embodiment of the invention.
Figure 17:
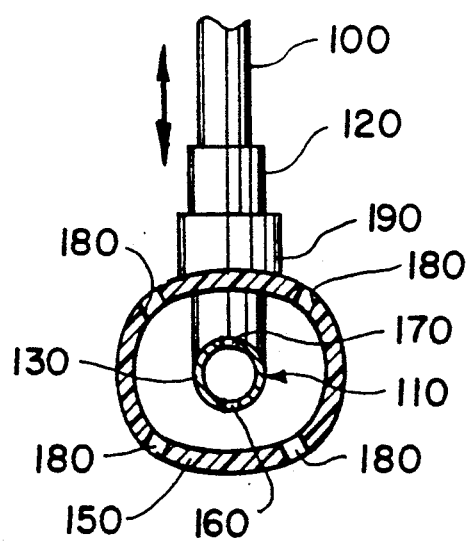
FIG. 17 is a cross-sectional view taken along line 17—17 of FIG. 16.

FIGS. 16 and 17 show an embodiment of the invention where the saliva discharge tube 100 is slidably mounted in a handle portion 120 connected to a water suction portion 130 of a water suction body 110 which is positioned within an ovoid, edge-less, smooth walled un-corrugated water collection body 150. Water suction portion 130 has openings 160 near its lower end which communicate with the interior of body 150 which has four rows of orifices 180. Portion 130 also has an upper air intake opening 170. Handle portion 120 is slidably and rotatably mounted in a mounting tube 190 forming part of the body 150. Tube 100 is also slidably and rotatably mounted within handle portion 120.

What is claimed is:

1. An instrument for discharging discharged water from the mouth during a dental treatment, comprising:
   an ovoid, smooth-surface, uncorrugated, edge-free hollow water collection body (150) having a front surface adapted to face outwardly of the mouth, and a rear surface adapted to face a throat inlet in the mouth, the water collection body being formed of soft resilient self-restoring material and having a long axis, wherein the shape of the water collection body is easily transformed when being pushed into the mouth to reduce a feeling of disorder in the mouth;
   the water collection body having a plurality of orifices extending in rows along the front and the rear surfaces of the water collection body and parallel to the axis;
   a mounting tube (190) projecting at an angle to the axis and from the water collection body, on one side of the front surface near one end of the water collection body with respect to the axis, the mounting tube communicating with the interior of the hollow water collection body;
   an L-shaped water suction body (110) having a handle portion (120) extending parallel to and into the mounting tube, and a water suction portion (130) extending in the water collection body and parallel to the axis of the water collection body, the water suction portion having a plurality of openings therein lying along the axis, a gap being provided between an outer periphery of the water suction portion and an inner periphery of the water collection body so that the shape of the water collection body can be transformed while still allowing the L-shaped water suction body to receive water from the water collection body; and
   a water discharge tube having one end slidable and rotatable in the handle portion for connecting the water discharge tube to the water collection body and the water suction body.

2. An instrument according to claim 1, wherein the water discharge tube is flexible for bending into a U-shape.

* * * * *